United States Patent [19]

Montagnier et al.

[11] Patent Number: 5,550,052
[45] Date of Patent: Aug. 27, 1996

[54] HYBRID CELL LINE FORMED BETWEEN T4 LYMPHOCYTES AND TUMORAL LYMPHOID TYPE CELLS

[75] Inventors: Luc Montagnier, Le Plessins Robinson; Françoise Rey, Paris; Bernard Krust, Paris; François Clavel, Paris, all of France

[73] Assignees: Institut Pasteur; Centre National de la Recherche Scientifique, both of France

[21] Appl. No.: 944,015

[22] Filed: Sep. 11, 1992

Related U.S. Application Data

[63] Continuation of Ser. No. 632,405, Dec. 20, 1990, which is a continuation of Ser. No. 221,303, Jul. 19, 1988, which is a continuation of Ser. No. 852,438, Apr. 15, 1986, abandoned, which is a continuation-in-part of Ser. No. 771,247, Aug. 31, 1985.

[30] Foreign Application Priority Data

Apr. 15, 1985 [FR] France .................. 85 05676

[51] Int. Cl.$^6$ .................................. C12N 5/22
[52] U.S. Cl. ............... 435/240.26; 435/240.1; 435/172.1; 435/172.2
[58] Field of Search ............... 935/95, 99, 101, 935/102; 435/240, 172.2

[56] References Cited

U.S. PATENT DOCUMENTS

| | | | |
|---|---|---|---|
| 4,591,552 | 5/1986 | Neurath | 436/534 |
| 4,629,783 | 12/1986 | Cosand | 530/324 |
| 4,665,032 | 5/1987 | Laurence | 435/240 |
| 4,675,295 | 6/1987 | Osawa et al. | 435/172.2 |
| 4,725,669 | 2/1988 | Essex et al. | 530/322 |

OTHER PUBLICATIONS

Le et al, "Human T cell hybridomas secreting immune interferon", *Proceedings of the National Academy of Science*, vol. 79, pp. 7857–7861, (Dec. 1982).

Klatzmann et al: "Selective Tropism of Lymphadenopathy Associated Virus (LAV) for Helper–Inducer T Lymphocytes" *Science* 225 pp. 59–63 (6 Jul. 1984).

Montagnier et al: Identification . . . Associated Virus Virology 144 (1985) 283–89.

Meusing et al "Nucleic Acid Structure and Expression of the Human AIDS/Lymphodenapathy Retrovirus", Nature, 313 (Feb. 7, 1985) 450–458.

Crowl et al, "HTLV–III Env Gene Products Synthesized in E. coli Are Recognized by Antibodies Present in the Sera of AIDS Patients", Cell, 44(Jul. 1985) 979–86.

Ratnes et al, "Complete Nucleotide Sequence of the AIDS Virus, HTLV–III", Nature, 313 (Jan. 24, 1985) 277–83.

Schupbach et al, "Antibodies to HTLV–III in Swiss Patients With AIDS and Pre–AIDS and in Groups at Risk for AIDS", New England J. Med., 312 (Jan. 31, 1985) 265–270.

Sanchez–Pescador et al, "Nucleotide Sequence and Expression of an AIDS–Associated Retrovirus (ARV–2)" Science, 227 (Feb. 1, 1985) 484–92.

Schneider et al, "A. Glycoprotein (Ogp 100) is the Main Antigen Detected by HTLV–III Antisera", Med. Microbiol. Immunol., 174 (1985) 35–42.

*Primary Examiner*—Christine M. Nucker
*Assistant Examiner*—Jeffrey Stucker
*Attorney, Agent, or Firm*—Finnegan, Henderson, Farabow, Garrett & Dunner

[57] ABSTRACT

The invention relates to new purified antigens of the LAV virus. They have molecular weights of about 135,000 and 150,000 daltons. They are useful for the detection of LAV antibodies in human sera. They are produced by hybrid cell-lines resulting from the fusion of T4 lymphocytes and cells of the MOLT-4 cell line.

5 Claims, 1 Drawing Sheet

HYBRID CELL LINE FORMED BETWEEN T4 LYMPHOCYTES AND TUMORAL LYMPHOID TYPE CELLS

This application is a continuation, of application Ser. No. 07/632,405, filed Dec. 20, 1990, which is a continuation of Ser. No. 221,303, filed Jul. 19, 1988, which is a continuation of Ser. No. 06/852,438, filed Apr. 15, 1988, now abandoned, which is a CIP of Ser. No. 06/771,247, filed Aug. 31, 1985.

The present invention relates to antigens of the envelope glycoprotein of the AIDS virus, particularly to precursors of this glycoprotein and to fragments of these antigens. It also relates to means for obtaining these antigens, precursors and fragments, as well as to applications of these antigens, precursors and fragments in the production of immunogenic compositions or to compositions useful for the diagnosis of AIDS or of infections which are related to AIDS, such as lymphadenopathies (LAS). More generally, the invention relates to the presence in a biological medium, such as human sera, of antibodies adapted to recognize selectively the LAV virus or viruses which are related to LAV. The preamble of the above said application, Ser. No. 771,247, refers to a number of scientific articles in which such related viruses have been described.

The patent application, Ser. No. 771,227, described an envelope glycoprotein having a molecular weight of about 110,000 daltons, designated below by the abbreviation "gp110". More particularly, gp110 has an apparent molecular weight of 110,000–120,000 daltons. It can be detected in lysates of LAV virus obtained from infected lymphocytes and labeled with $^{35}S$-cysteine. This glycoprotein is selectively recognized by sera of patients afflicted with LAS or AIDS.

The present invention comprises different antigens related to gp110, either precursors, or fragments of gp110, and novel means (cellular strains and methods) enabling these antigens to be obtained, including gp110.

Accordingly, the invention relates to glycoproteins having molecular weights of approximately 150,000 and 135,000 daltons (molecular weights were evaluated by measurement of the migration distances of the glycoproteins and by comparing the migration distances with those of reference proteins and of known molecular weights, such as those which have been identified in French patent application No. 85 05676, filed Apr. 15, 1985). The novel glycoproteins also have the following properties characteristic of gp110:
capability of being labeled with $^{35}S$-cysteine,
capability of forming complexes with concanavaline A, these complexes being dissociated by O-methyl-alpha-D-mannopyranoside,
capability of forming complexes with other lectins, such as those known under the designation LENTYL LECTINES™,
sensitivity to endoglycosidases, particularly endo-beta-methylglycosaminidase-H (in abbreviated form: endo-H),
capability of being labeled with [$^{14}C$]-glucosamine,
capability of being recognized selectively by sera of persons infected with AIDS or LAS.

In the following description, the glycoproteins of molecular weights 150,000 and 135,000 daltons are denoted by the abbreviations "gp150" and "gp135", respectively.

The structure of the polypeptide skeleton of gp150 seems to be correlated to the structure produced by the complete nucleotide sequence of the "env" gene. The nucleotide sequence can be deduced from the article of Wain-Hobson et al., Cell, 40, 9–17 (1985). This polypeptide skeleton has an apparent molecular weight of approximately 90,000 daltons. It appears to correspond to the polypeptide sequence coded by the nucleotide sequence extending between position 5767 and position 8350, as indicated by the nucleotide sequence of FIG. 1 of the article of Wain-Hobson et al.

The glycoprotein gp135 appears to correspond to a shorter polypeptide skeleton, derived from a preceding polypeptide skeleton, following a proteolytic cleavage of a terminal peptide sequence having a molecular weight of about 15,000 daltons. The glycoprotein gp135 appears to correspond to the C-terminal portion of the peptide skeleton of gp150.

The invention also relates to means enabling the production of considerable amounts of the precursors, in particular, cellular hybrids formed between normal T4 lymphocytes and cells of the MOLT-4 line, described by, for example, Minowada et al., J. Natl. Cancer Inst., 49, 891 (1972), or the like. The cellular hybrids are characterized by their capacity to express the T4 molecule at their surface and by their susceptibility to infection by LAV or related viruses.

It is noted that cells of the MOLT-4 line are derived from cells of a lymphoid type which have been isolated from a patient afflicted with leukemia.

The hybrids are capable of principally producing proteins encoded by the viral genome resulting from infection by a LAV virus. This enables the possibility of recovering appreciable amounts of said proteins and of studying the development of the relative proportions of each protein in the course of the viral cycle. The description given below provides the conditions for which such studies have been conducted.

These hybrids may particularly be made as follows:

T4 lymphocytes of a blood donor are separated according to the technique described by Klatzman et al., Nature, 312 767 (1984). The lymphocytes are then fused with cells of a MOLT-4/TK line in the presence of polyethyleneglycol by conventional techniques for the production of hybridomas. The hybrids formed are selected in HAT medium in cups of a microtitration plate. The clones which express the T4 molecule at their surface are collected. The clones can be more particularly recognized by the monoclonal antibodies marketed by the ORTHO company under the trade name OKT4™.

A line of MOLT-4/TK cells, from which the above said cellular hybrids can be formed, has been deposited at the Collection Nationale de Culture de Micro-Organismes (C.N.C.M.), Institut Pasteur, 28 rue du Docteur Roux, 75724 Paris Cedex 15, on Apr. 15, 1985, under n° I-434.

It is self-evident that it is possible to use in place of the MOLT-4/TK lines, any other MOLT-4 mutant showing a genetic deficiency which is capable of being complemented by T4 lymphocytes during cellular fusion. This complementation provides an adequate basis for selection of the desired hybrids.

A hybrid representative of the hybrids according to the invention has been deposited at the C.N.C.M., on Apr. 15, 1985, under n° I-435. Such hybrids can be cultivated in the medium described by, for example, Minowata et al.

After concentration by centrifugation, selected cellular hybrids, particularly like that described above, can be infected with LAV or related virus or the like according to the technique in the above said French patent application No. 85 05676, filed Apr. 15, 1985. In particular, this process comprises resuspension of the cellular hybrids in the infectious viral supernatant liquor, produced by normal lymphocytes previously infected by an isolate of LAV obtained from a patient afflicted with LAS or AIDS. This process has been described by Barre-Sinoussi et al., Science, 220, 868 (1983), and in European patent application No. 84 401834, filed Sep. 14, 1984, with priority of British Application No. 83 24800, filed Sep. 15, 1983.

After infection by a LAV virus, such as LAV1 in the above said European patent application, the hybrid cells produce polycarions or giant syncitias resulting from fusions between infected hybrid cells or between uninfected and infected hybrid cells. These giant syncitias produce, particularly after fixation by acetone, strong immunofluorescence reactions in indirect immunofluorescence tests with sera from carriers of anti-LAV antibodies. The syncitias can easily be isolated, particularly by simple decantation under the effect of gravity in the culture medium or in the medium it is resuspended in.

The technique above has enabled, under conditions which will be described below, the observation of the periods of the viral cycle at which the glycoprotein precursors appear. The precursors can be isolated under the conditions described below in the legend for FIG. 1.

It will be shown that gp150 appears as a single band in the first hours of viral infection, for example, after 3 hours. The glycoproteins gp135 appears later, particularly after 12 hours.

The conditions in which gp110 appears, and its relationship with other antigens which can be isolated, is described below. In particular, refer to the legend of FIG. 2.

Described below are conditions in which gp150 and gp135 have been detected from syncitias infected under the above indicated conditions.

After labeling for periods of 3 or 12 hours, the syncitias were lysed in a detergent solution and the clarified lysate was immunoprecipitated with a denatured, LAV-positive serum. The lysate was then analyzed by electrophoresis on a sodium dodecylsulfate gel (SDS). After 3 hours of labeling, a band of molecular weight 150,000 (150K) was detected. After 12 hours of labeling another band of 135K appeared. This band was derived from the precursor 150K. A band of 110K–120K was not detected. This fact confirms that gp110 is associated with free viral particles and not with the virus in the course of formation.

After treatment with endo-H, bands of 150K and 135K were reduced to two bands having respectively molecular weights of 95,000 (95K) and 80,000 (80K), respectively (FIG. 1). The following hypothesis can be formulated, with the reservation of additional study: the precursor gp150 corresponds to the total coding sequence of the envelope gene described above. This precursor also corresponds to the polypeptide chain of 95K, which has had carbohydrate groups removed corresponds to the total coding sequence of the envelope gene as deduced from the sequence of the viral genome described above.

After the first proteolytic cleavage, which seems to take place either in the cytoplasm or close to the cellular membrane, gp150 is transformed into gp135 (to which a polypeptide skeleton of 80K corresponds after separation of the carbohydrate groups). In the course of the morphogenesis of the virus, gp135 is transformed into gp110–gp120, as a result of the partial enzymatic removal of carbohydrate groups in the absence of proteolytic cleavage.

The glycoproteins gp150 and gp135 can also be obtained from corresponding syncitia lysates by the same technique as indicated in regard to gp110 in the above said French patent application No. 85 05676, filed Apr. 15, 1985.

Similarly, it is noted that the techniques of producing antibodies, more particularly monoclonal antibodies, described in Ser. No. 771,247, filed Aug. 31, 1985, with respect to the isolation of gp110, can be applied under similar conditions to the production of antibodies, more particularly of specific monoclonal antibodies of gp150 and of gp135. These monoclonal antibodies, particularly after immobilization on an adequate support and under the same conditions as mentioned in Ser. No. 771,247, filed Aug. 31, 1985, in regard to gp110, can be used for a more thorough purification of gp150 and of gp135.

In the same manner as has been described for gp110 in Ser. No. 771,247, filed on Aug. 31, 1985, gp150 and gp135 can be used, under similar conditions, for the production of immunogenic compositions. In particular, the invention relates to immunogenic compositions containing antigens according to the present invention in association with a physiologically acceptable vehicle enabling its administration to a living host, particularly man. Such a composition is, for example, characterized in that it is dosed with antigen so as to permit the administration of unit doses of 10 to 500, particularly from 50 to 100 micrograms/kg.

Again, under the same conditions as those mentioned with respect to gp110 in Ser. No. 771,247, gp150 and gp135 can be employed in diagnostic methods and "kits" for the detection of anti-LAV antibodies in an adequate biological medium, particularly the serum or the cerebro-spinal fluid of patients afflicted with diseases caused by the LAV or related viruses, or persons immunized against these viruses. The use of gp150 or of gp135 in diagnostic tests or "kits" can be established as particularly advantageous with respect to sera which can recognize them, in particular gp150. Reference is again made to the description of French patent application No. 85 05767, filed Apr. 15, 1985, as to the conditions under which the diagnostic methods and "kits" can be employed. Reference is also made to the claims of the present application which, besides defining preferred forms of the diagnostic processes and "kits" of the invention, are to be considered as forming an integral part of the description.

The cellular hybrids which express on their surface gp150, or both gp150 and gp135, also form part of the invention. These cellular hybrids can, particularly when they are in a fixed state, form part of diagnostic "kits". A diagnostic method comprises contacting cellular hybrids comprising the glycoproteins or glycoprotein fragments previously fixed, for example, by acetone or any adequate fixation solution, with sera of the above indicated patients. The glycoproteins or glycoprotein fragments are detected by employing conventional methods, particularly by means of human anti-immunoglobulins or labeled antibodies of mice (radioactive, enzymatic, fluorescent, etc. labels).

The following data is provided in regard to gp110, its properties and its relationship to other antigens which can be isolated from lymphocyte cultures or CEM cells infected with the LAV virus (LAV1 in the description which follows). The CEM cells used were derived from the ATCC CCL 19 line of strains (deposited Jan. 29, 1985, at the C.N.C.M., under numbers I-416 and I-417) which have been found to possess T4 molecules at their surface.

In particular, data has been obtained employing the following procedure.

T lymphocytes from a normal donor and CEM cells were infected with the LAV1 virus and labeled with $^{35}$S-cysteine in a medium free of unlabeled cysteine. The clarified supernatant liquor from the cell culture was then treated by centrifugation, as described in the French patent application, Ser. No. 85 05767, filed Apr. 15, 1985. The supernatant liquor is then subjected to lysis in a RIPA buffer and incubated with human sera obtained from persons which are either infected or uninfected with LAV.

The virus lysates, analyzed according to the legend of FIG. 2, are detected by sera from patients infected with AIDS. After gelelectrophoresis, fine bands of the above said lysates of proteins having molecular weights of about 70K, 40K and 34K respectively, in addition to gp110, are immunoprecipitated by sera of said patients. As these sera do not recognize any gag protein, it may be presumed that these proteins are antigenically related to gp110 and that they are cleavage products of gp110. The bands are more pronounced after they are transferred to filter paper by "immunoblotting" to which reference is made in the legend of FIG. 2.

Similar results were obtained when cultures of infected T lymphocytes were metabolically labeled with [$^{14}$C]-glucosamine. The previously centrifuged lysates of the virus have also produced immunoprecipitation bands with a LAV-positive serum in tests carried out on a polyacrylamide gel containing SDS (SDS-PAGE). In addition to the bands specifically recognized by said sera at the level of gp110, immunoprecipitations at the level of bands of 70K and 42K were observed.

The fact that the proteins of 70K and 40K are probably cleavage products of gp110 is also confirmed by an examination of the nucleotide sequence of the viral genome, which shows a potential proteolytic site at the level of the second third of the env gene. Apparently, the protein of 40K corresponds to the transmembrane portion of the envelope glycoprotein.

Referring again to the nucleotide sequence of the article of Wain-Hobson et al., it appears that the proteins of 70K and 40K have polypeptide sequences in common with the polypeptides which are coded by the nucleotide sequences extending:

between position 5767 and approximately position 7297–7327 for the protein of 70K, and between approximately position 7297–7327 and position 8350 for the protein of 40K.

The proteins of 70K and 40K therefore form part of the invention. As with the glycoproteins gp110, gp135, and gp150, they can be used in diagnostic methods and "kits" which have been described with respect to gp110, gp135, and gp150.

It is self-evident that the invention relates to polypeptides equivalent to those which have been described in this patent application (whether or not these polypeptides possess carbohydrate groups), particularly polypeptides having similar amino acid sequences and produced by employing genetic engineering techniques. It is also self-evident that polypeptides which differ from those which have been described by their amino acid sequences without substantial modification of their immunological properties, must be considered as encompassed by the scope of the claims. In this respect, the invention relates to equivalent polypeptides obtained from species of LAV virus other than that which has been employed in the present application.

DESCRIPTION OF THE DRAWINGS

Description of FIG. 1: Effect of endo-H on the envelope glycoprotein of LAV and its cellular precursors.

Lysates of syncitia hybridomas MOLT-4/T4 infected with LAV and labeled for 12 hours with $^{35}$S-cysteine (columns a to d) and of LAV virions labeled with $^{35}$S-cysteine, separated by centrifugation (columns e to h), were immunoprecipitated with serum of a patient (BRU) suffering from persistant lymphadenopathy. The immune complexes were coupled to agarose beads, marketed under the trademark SEPHAROSE™, to which protein A was coupled. The immune complexes were then washed several times and eluted by heating to 95° C. for two minutes in a citrate buffer, pH 5.5, containing 0.1% SDS and 5% of aprotinin (ZYMOFREN, SPECIA). The solubilized antigens were then treated with 0.5 microgram of endo-H in a final volume of 22 microliters over different durations at 37° C. Finally, they were analyzed by electrophoresis on a SDS-polyacrylamide gel (7.5% of acrylamide and 0.17% of bisacrylamide).

The following observations are noted:
columns a and e: no treatment;
columns b and f: 1 hour of treatment;
columns c and g: 2 hours of treatment;
columns d and h: 3 hours of treatment;
m=label of known molecular weights.

Figure 1:
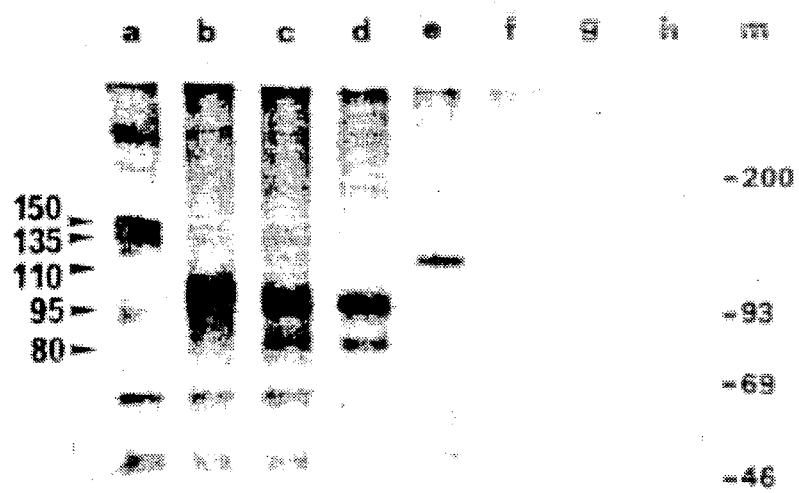
Figure 2:
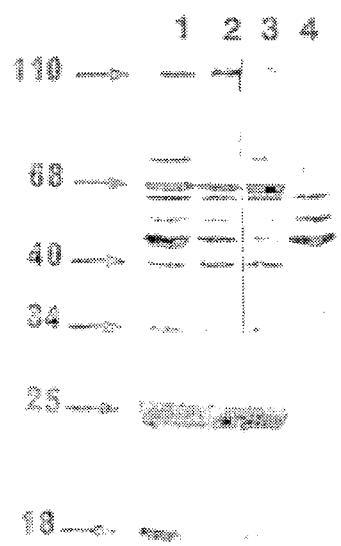

Description of FIG. 2: Analysis by the "Western blot" technique.

The supernatant liquors from cells infected with LAV and from cells infected with HTLV-3 were concentrated by ultracentrifugation. The centrifugation pellets obtained from viral preparations and from control preparations (whereby these pellets had a total protein concentration of 5 to 10 grams) were fractionated on a 12% polyacrylamide gel containing SDS, transferred electrophoretically to sheets of nitrocellulose, and then transferred by immunotransfer (immunoblot) as described by Parekh B., et al., *Virology*, 107, 520 (1980). The filter paper comprising the bands was then incubated with serum of a patient afflicted with LAS (diluted to 1/200), washed, incubated with goat anti-human IgG, coupled with peroxidase, and again washed. The detection of the antibodies employed diamino-benzidine as the substrate for the peroxidase reaction. Similar observations were made with virus lysates obtained from H9 cells infected with LAV or HTLV-III.

The following observations are noted:
column 1: viral pellet obtained from H9 cells infected with LAV;
column 2: viral pellet obtained from H9 cells infected with HTLV-III;
column 3: viral pellet obtained from CEM cells which produce LAV;
column 4: viral pellet obtained from uninfected H9 cells;
the arrows identify from top to bottom the bands corresponding to the following glycoproteins or proteins: gp110, p70, p40, p34, p25 and p18.

We claim:

1. A hybrid cell line, wherein the hybrid cells are formed between human T4 lymphocytes and a MOLT-4 cell, wherein said hybrid cells express T4 molecule at their surface; and said hybrid cells are infected by a human immunodeficiency virus type 1 (HIV-1).

2. A hybrid cell line deposited with the National Collection of Cultures of Microorganisms or Collection Nationale de Cultures de Micro-organismes ("C.N.C.M.") under Accession No. 1-435.

3. A hybrid cell line, wherein the hybrid cells are formed between human T4 lymphocytes and a MOLT-4 cell, wherein said hybrid cells express T4 molecule at their surface, said hybrid cells are infected by a human immunodeficiency virus type 1 (HIV-1), and said cell line carries at its surface an envelope antigen of HIV-1, wherein said antigen has a molecular weight of about 150,000 daltons;

is recognized by sera of patients infected with an HIV-1 virus;

can be labeled with $^{35}$S-cysteine;

forms complexes with concanavalin A, wherein said complexes are dissociated by O-methyl-alpha-D-mannopyranoside;

forms complexes with lectins;

can be labeled with $^{14}$C-glucosamine; and forms a protein with a molecular weight of about 95,000 daltons after exposure to an endoglycosidase H.

4. A hybrid cell line, wherein the hybrid cells are formed between human T4 lymphocytes and a MOLT-4 cell, wherein said hybrid cells express T4 molecule at their surface, said hybrid cells are infected by a human immunodeficiency virus type 1 (HIV-1), and said cell line carries at its surface an envelope antigen of HIV-1, wherein said antigen has a molecular weight of about 135,000 daltons;

is recognized by sera of patients infected with an HIV-1 virus;

can be labeled with $^{35}$S-cysteine;

forms complexes with concanavalin A, wherein said complexes are dissociated by O-methyl-alpha-D-mannopyranoside;

forms complexes with lectins;

can be labeled with $^{14}$C-glucosamine; and forms a protein with a molecular weight of about 80,000 daltons after exposure to an endoglycosidase H.

5. The hybrid cell line according to claim 3, wherein said antigen is encoded by the nucleic acid corresponding to the envelope gene of HIV-1, which extends from about nucleotide 5767 to about nucleotide 8350 of the genome of HIV-1, said nucleic acid having the following sequence:

```
       5770        5780        5790        5800        5810
       ATGA  GAGTGAAGGA  GAAATATCAG  CACTTGTGGA  GATGGGGGTG 5820        5830        5840        5850        5860
 GAAATGGGGC  ACCATGCTCC  TTGGGATATT  GATGATCTGT  AGTGCTACAG 5870        5880        5890        5900        5910
 AAAAATTGTG  GGTCACAGTC  TATTATGGGG  TACCTGTGTG  GAAGGAAGCA 5920        5930        5940        5950        5960
 ACCACCACTC  TATTTTGTGC  ATCAGATGCT  AAAGCATATG  ATACAGAGGT 5970        5980        5990        6000        6010
 ACATAATGTT  TGGGCCACAC  ATGCCTGTGT  ACCCACAGAC  CCCAACCCAC 6020        6030        6040        6050        6060
 AAGAAGTAGT  ATTGGTAAAT  GTGACAGAAA  ATTTTAACAT  GTGGAAAAAT 6070        6080        6090        6100        6110
 GACATGGTAG  AACAGATGCA  TGAGGATATA  ATCAGTTTAT  GGGATCAAAG 6120        6130        6140        6150        6160
 CCTAAAGCCA  TGTGTAAAAT  TAACCCCACT  CTGTGTTAGT  TTAAAGTGCA 6170        6180        6190        6200        6210
 CTGATTTGGG  GAATGCTACT  AATACCAATA  GTAGTAATAC  CAATAGTAGT 6220        6230        6240        6250        6260
 AGCGGGGAAA  TGATGATGGA  GAAAGGAGAG  ATAAAAAACT  GCTCTTTCAA 6270        6280        6290        6300        6310
 TATCAGCACA  AGCATAAGAG  GTAAGGTGCA  GAAAGAATAT  GCATTTTTTT 6320        6330        6340        6350        6360
 ATAAACTTGA  TATAATACCA  ATAGATAATG  ATACTACCAG  CTATACGTTG 6370        6380        6390        6400        6410
 ACAAGTTGTA  ACACCTCAGT  CATTACACAG  GCCTGTCCAA  AGGTATCCTT 6420        6430        6440        6450        6460
 TGAGCCAATT  CCCATACATT  ATTGTGCCCC  GGCTGGTTTT  GCGATTCTAA 6470        6480        6490        6500        6510
 AATGTAATAA  TAAGACGTTC  AATGGAACAG  GACCATGTAC  AAATGTCAGC 6520        6530        6540        6550        6560
 ACAGTACAAT  GTACACATGG  AATTAGGCCA  GTAGTATCAA  CTCAACTGCT 6570        6580        6590        6600        6610
 GTTGAATGGC  AGTCTAGCAG  AAGAAGAGGT  AGTAATTAGA  TCTGCCAATT 6620        6630        6640        6650        6660
 TCACAGACAA  TGCTAAAACC  ATAATAGTAC  AGCTGAACCA  ATCTGTAGAA 6670        6680        6690        6700        6710
 ATTAATTGTA  CAAGACCCAA  CAACAATACA  AGAAAAAGTA  TCCGTATCCA 6720        6730        6740        6750        6760
 GAGGGGACCA  GGGAGAGCAT  TTGTTACAAT  AGGAAAAATA  GGAAATATGA 6770        6780        6790        6800        6810
 GACAAGCACA  TTGTAACATT  AGTAGAGCAA  AATGGAATGC  CACTTTAAAA 6820        6830        6840        6850        6860
 CAGATAGCTA  GCAAATTAAG  AGAACAATTT  GGAAATAATA  AAACAATAAT 6870        6880        6890        6900        6910
 CTTTAAGCAA  TCCTCAGGAG  GGGACCCAGA  AATTGTAACG  CACAGTTTTA 6920        6930        6940        6950        6960
 ATTGTGGAGG  GGAATTTTTC  TACTGTAATT  CAACACAACT  GTTTAATAGT 6970        6980        6990        7000        7010
 ACTTGGTTTA  ATAGTACTTG  GAGTACTGAA  GGGTCAAATA  ACACTGAAGG 7020        7030        7040        7050        7060
 AAGTGACACA  ATCACACTCC  CATGCAGAAT  AAAACAATTT  ATAAACATGT
```

-continued

```
            7070       7080       7090       7100       7110
     GGCAGGAAGT AGGAAAAGCA ATGTATGCCC CTCCCATCAG CGGACAAATT 7120       7130       7140       7150       7160
     AGATGTTCAT CAAATATTAC AGGGCTGCTA TTAACAAGAG ATGGTGGTAA 7170       7180       7190       7200       7210
     TAACAACAAT GGGTCCGAGA TCTTCAGACC TGGAGGAGGA GATATGAGGG 7220       7230       7240       7250       7260
     ACAATTGGAG AAGTGAATTA TATAAATATA AAGTAGTAAA AATTGAACCA 7270       7280       7290       7300       7310
     TTAGGAGTAG CACCCACCAA GGCAAAGAGA AGAGTGGTGC AGAGAGAAAA 7320       7330       7340       7350       7360
     AAGAGCAGTG GGAATAGGAG CTTTGTTCCT TGGGTTCTTG GGAGCAGCAG 7370       7380       7390       7400       7410
     GAAGCACTAT GGGCGCACGG TCAATGACGC TGACGGTACA GGCCAGACAA 7420       7430       7440       7450       7460
     TTATTGTCTG GTATAGTGCA GCAGCAGAAC AATTTGCTGA GGGCTATTGA 7470       7480       7490       7500       7510
     GGCGCAACAG CATCTGTTGC AACTCACAGT CTGGGCATC AAGCAGCTCC 7520       7530       7540       7550       7560
     AGGCAAGAAT CCTGGCTGTG GAAAGATACC TAAAGGATCA ACAGCTCCTG 7570       7580       7590       7600       7610
     GGGATTTGGG GTTGCTCTGG AAAACTCATT TGCACCACTG CTGTGCCTTG 7620       7630       7640       7650       7660
     GAATGCTAGT TGGAGTAATA AATCTCTGGA ACAGATTTGG AATAACATGA 7670       7680       7690       7700       7710
     CCTGGATGGA GTGGGACAGA GAAATTAACA ATTACACAAG CTTAATACAT 7720       7730       7740       7750       7760
     TCCTTAATTG AAGAATCGAA AACCAGCAAG AAAAGAATGA ACAAGAATTA 7770       7780       7790       7800       7810
     TTGGAATTAG ATAAATGGGC AAGTTTGTGG AATTGGTTTA ACATAACAAA 7820       7830       7840       7850       7860
     TTGGCTGTGG TATATAAAAA TATTCATAAT GATAGTAGGA GGCTTGGTAG 7870       7880       7890       7900       7910
     GTTTAAGAAT AGTTTTTGCT GTACTTTCTA TAGTGAATAG AGTTAGGCAG 7920       7930       7940       7950       7960
     GGATATTCAC CATTATCGTT TCAGACCCAC CTCCCAACCC CGAGGGGACC 7970       7980       7990       8000       8010
     CGACAGGCCC GAAGGAATAG AAGAAGAAGG TGGAGAGAGA GACAGAGACA 8020       8030       8040       8050       8060
     GATCCATTCG ATTAGTGAAC GGATCCTTAG CACTTATCTG GGACGATCTG 8070       8080       8090       8100       8110
     CGGAGCCTTG TGCCTCTTCA GCTACCACCG CTTGAGAGAC TTACTCTTGA 8120       8130       8140       8150       8160
     TTGTAACGAG GATTGTGGAA CTTCTGGGAC GCAGGGGGTG GGAAGCCCTC 8170       8180       8190       8200       8210
     AAATATTGGT GGAATCTCCT ACAGTATTGG AGTCAGGAAC TAAAGAATAG 8220       8230       8240       8250       8260
     TGCTGTTAGC TTGCTCAATG CCACAGCCAT AGCAGTAGCT GAGGGGACAG 8270       8280       8290       8300       8310
     ATAGGGTTAT AGAAGTAGTA CAAGGAGCTT GTAGAGCTAT TCGCCACATA 8320       8330       8340       8350
     CCTAGAAGAA TAAGACAGGG CTTGGAAAGG ATTTTGCTA.
```

\* \* \* \* \*